(12) United States Patent
Ko et al.

(10) Patent No.: US 10,779,766 B2
(45) Date of Patent: Sep. 22, 2020

(54) WEARABLE MEASUREMENT APPARATUS

(71) Applicant: SAMSUNG ELECTRONICS CO., LTD., Suwon-si (KR)

(72) Inventors: Byung Hoon Ko, Hwaseong-si (KR); Yong Joo Kwon, Yongin-si (KR); Youn Ho Kim, Hwaseong-si (KR); Sang Yun Park, Hwaseong-si (KR); Jin Hyun Yun, Seoul (KR); Jong Wook Lee, Suwon-si (KR); Chang Mok Choi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 221 days.

(21) Appl. No.: 15/426,153

(22) Filed: Feb. 7, 2017

(65) Prior Publication Data

US 2018/0055449 A1 Mar. 1, 2018

(30) Foreign Application Priority Data

Aug. 31, 2016 (KR) .......................... 10-2016-0111833

(51) Int. Cl.
*A61B 5/00* (2006.01)
*A61B 5/0205* (2006.01)
(Continued)

(52) U.S. Cl.
CPC .............. *A61B 5/6843* (2013.01); *A61B 5/01* (2013.01); *A61B 5/021* (2013.01); *A61B 5/0205* (2013.01);
(Continued)

(58) Field of Classification Search
CPC ... A61B 5/6843; A61B 5/6844; A61B 5/6831; A61B 5/6824; A61B 5/681;
(Continued)

(56) References Cited

U.S. PATENT DOCUMENTS

| 8,246,547 | B2 | 8/2012 | Phua et al. |
| 9,113,795 | B2 | 8/2015 | Hong et al. |
| 2007/0293781 | A1* | 12/2007 | Sims ..................... A61B 5/1135 600/534 |
| 2014/0361147 | A1* | 12/2014 | Fei ........................ G01J 1/0407 250/206 |

(Continued)

FOREIGN PATENT DOCUMENTS

| JP | 2015-154945 A | 8/2015 |
| KR | 10-1304549 B1 | 9/2013 |

(Continued)

*Primary Examiner* — Matthew Kremer
*Assistant Examiner* — Avery M Foley
(74) *Attorney, Agent, or Firm* — Sughrue Mion, PLLC

(57) ABSTRACT

A wearable measurement apparatus capable of measuring a biometric signal is provided. The wearable measurement apparatus includes a main body, and a main-body elastic part disposed on a bottom surface of the main body, and configured to elastically support the main body against a body part of a user. The wearable measurement apparatus further includes a biometric signal sensor disposed apart from the main-body elastic part, and configured to detect a biometric signal from the body part, and a sensor elastic part interposed between the main body and the biometric signal sensor, and configured to form a step difference between a bottom surface of the biometric signal sensor and a bottom surface of the main-body elastic part, and elastically support the biometric signal sensor against the main body.

22 Claims, 9 Drawing Sheets

(51) Int. Cl.
*A61B 5/01* (2006.01)
*A61B 5/021* (2006.01)
*A61B 5/024* (2006.01)
*A61B 5/0295* (2006.01)
*A61B 5/0402* (2006.01)
*A61B 5/0488* (2006.01)
*A61B 5/08* (2006.01)
*G01L 5/00* (2006.01)

(52) U.S. Cl.
CPC ........ *A61B 5/0295* (2013.01); *A61B 5/02438* (2013.01); *A61B 5/0402* (2013.01); *A61B 5/0488* (2013.01); *A61B 5/0816* (2013.01); *A61B 5/681* (2013.01); *A61B 5/6831* (2013.01); *A61B 5/6832* (2013.01); *G01L 5/0038* (2013.01)

(58) Field of Classification Search
CPC ....... A61B 5/6802; A61B 5/6801; A61B 5/68; A61B 5/01; A61B 5/0205; A61B 5/02438; A61B 5/0245; A61B 5/021; A61B 5/0402; A61B 5/0488; A61B 5/0816; A61B 5/6832; G01L 5/0038
See application file for complete search history.

(56) References Cited

U.S. PATENT DOCUMENTS

| | | | |
|---|---|---|---|
| 2015/0031964 A1* | 1/2015 | Bly | A61B 5/7465 600/301 |
| 2015/0201854 A1* | 7/2015 | Hong | A61B 5/02427 600/301 |
| 2015/0265214 A1* | 9/2015 | De Kok | A61B 5/6843 600/301 |
| 2015/0366475 A1 | 12/2015 | Just et al. | |
| 2016/0041531 A1* | 2/2016 | MacKie | A61B 5/0059 368/80 |
| 2016/0045135 A1 | 2/2016 | Kim et al. | |
| 2016/0073886 A1* | 3/2016 | Connor | G09B 19/0092 600/475 |
| 2016/0198996 A1* | 7/2016 | Dullen | A61B 5/0024 600/301 |
| 2017/0020399 A1* | 1/2017 | Shemesh | A61B 5/0205 |

FOREIGN PATENT DOCUMENTS

| | | |
|---|---|---|
| KR | 10-1382707 B1 | 4/2014 |
| KR | 10-2015-0109971 A | 10/2015 |
| KR | 10-2015-0110413 A | 10/2015 |
| KR | 10-2016-0021713 A | 2/2016 |

\* cited by examiner

WEARABLE MEASUREMENT APPARATUS

CROSS-REFERENCE TO RELATED APPLICATION

This application claims priority from Korean Patent Application No. 10-2016-0111833, filed on Aug. 31, 2016, in the Korean Intellectual Property Office, the disclosure of which is incorporated herein by reference in its entirety.

BACKGROUND

1. Field

Apparatuses consistent with exemplary embodiments relate to a wearable measurement apparatus for measuring a biometric signal.

2. Description of Related Art

With the advancement of technologies, electronic devices have been reduced in size and weight, allowing for various shapes, and as a result, various types of wearable devices that can be put on a human body part have been developed. For example, a wearable device includes a smart watch. The smart watch has a variety of features, as well as a watch feature for providing time information, and may include, for example, an embedded system wristwatch.

Because the wearable device is put on a wearer's body part, a biometric signal may be acquired. Accordingly, many types of wearable devices equipped with various sensors have been developed. For example, the wearable device may include a blood glucose sensor, a blood pressure sensor, or the like. In addition, the wearable device may include a diversity of sensors, such as a biosensor, a motion sensor, a chemical sensor, a temperature sensor, and a position sensor.

The biosensor refers to a device used to measure the state or density of organic compounds using capabilities of living organisms. The motion sensor refers to a device used to detect a motion of a device. For example, the motion sensor may include a gyroscope or an acceleration sensor. The chemical sensor refers to a sensor that deals with chemical materials. The temperature sensor refers to a device used to measure a temperature. The position sensor refers to a device used to measure a position, such as a global positioning system (GPS).

SUMMARY

Exemplary embodiments may address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a wearable measurement apparatus including a main body, and a main-body elastic part disposed on a bottom surface of the main body, and configured to elastically support the main body against a body part of a user. The wearable measurement apparatus further includes a biometric signal sensor disposed apart from the main-body elastic part, and configured to detect a biometric signal from the body part, and a sensor elastic part interposed between the main body and the biometric signal sensor, and configured to form a step difference between a bottom surface of the biometric signal sensor and a bottom surface of the main-body elastic part, and elastically support the biometric signal sensor against the main body.

The sensor elastic part may be formed such that the bottom surface of the biometric signal sensor is positioned lower than the bottom surface of the main-body elastic part.

The main-body elastic part may have a modulus of elasticity greater than a modulus of elasticity of the sensor elastic part.

The wearable measurement apparatus may further include a strap connected to the main body, and configured to allow the wearable measurement apparatus to be disposed on the body part.

The wearable measurement apparatus may further include a compression sensor configured to measure a pressing force that is exerted on the body part when the biometric signal sensor is in contact with the body part.

The wearable measurement apparatus may further include a controller, the compression sensor may include a displacement sensor configured to measure a displacement of the sensor elastic part and a displacement of the main-body elastic part, and the controller may be configured to determine the pressing force, based on the measured displacement of the sensor elastic part, the measured displacement of the main-body elastic part, a modulus of elasticity of the sensor elastic part, and a modulus of elasticity of the main-body elastic part.

The wearable measurement apparatus may further include a display configured to display the pressing force.

The wearable measurement apparatus may further include a controller configured to determine whether the biometric signal is within a normal range.

The wearable measurement apparatus may further include a step-difference control portion configured to adjust the step difference between the bottom surface of the biometric signal sensor and the bottom surface of the main-body elastic part.

The main-body elastic part may include a first main-body elastic part and a second main-body elastic part, and a bottom surface of the first main-body elastic part and a bottom surface of the second main-body elastic part may be at different heights.

The sensor elastic part may be formed such that the bottom surface of the biometric signal sensor is positioned higher than the bottom surface of the main-body elastic part.

The wearable measurement apparatus may further include an adhesive member disposed on the bottom surface of the biometric signal sensor, and configured to attach the biometric signal sensor to the body part.

The main-body elastic part may have a modulus of elasticity greater than a modulus of elasticity of the sensor elastic part.

The wearable measurement apparatus may further include a strap connected to the main body, and configured to allow the wearable measurement apparatus to be disposed on the body part.

The wearable measurement apparatus may further include an adsorption sensor configured to measure an adsorption force that is imposed on the body part when the biometric signal sensor is in contact with the body part.

The wearable measurement apparatus may further include a controller, the adsorption sensor may include a displacement sensor configured to measure a displacement of the sensor elastic part and a displacement of the main-body elastic part, and the controller may be configured to determine the adsorption force, based on the measured displacement of the sensor elastic part, the measured displacement of the main-body elastic part, a modulus of elasticity of the sensor elastic part, and a modulus of elasticity of the main-body elastic part.

The wearable measurement apparatus may further include a display configured to display the adsorption force.

The wearable measurement apparatus may further include a controller configured to determine whether the biometric signal is within a normal range.

The wearable measurement apparatus may further include a step-difference control portion configured to adjust the step difference between the bottom surface of the biometric signal sensor and the bottom surface of the main-body elastic part.

BRIEF DESCRIPTION OF THE DRAWINGS

The above and/or other aspects will be more apparent by describing exemplary embodiments with reference to the accompanying drawings.

DETAILED DESCRIPTION

Figure 1:
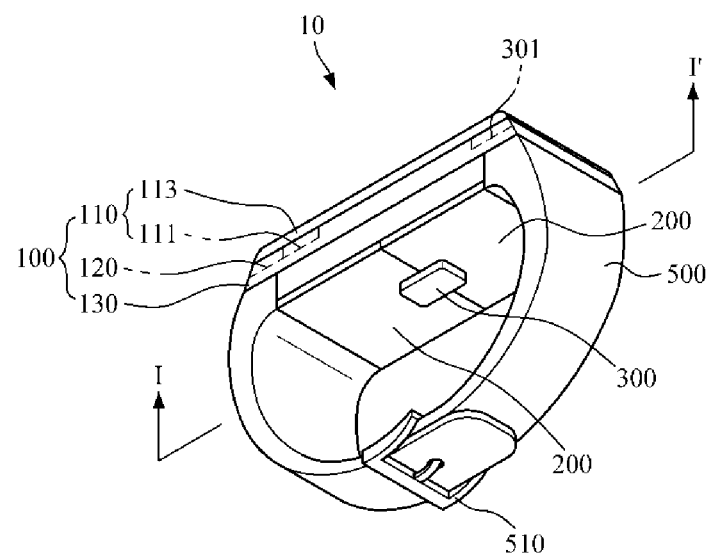
FIG. 1 is a perspective view of a wearable measurement apparatus according to an exemplary embodiment.

Exemplary embodiments are described in greater detail with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

Hereinafter, exemplary embodiments will be described under the assumption that a wearable measurement apparatus 10 is a smart watch worn on a wearer's body part 20, especially, a wrist, but the exemplary embodiments are not limited thereto, such that the wearable measurement apparatus 10 is any type of device that is attached to the wearer's body part 20 to measure a biometric signal. In another example, the wearable measurement apparatus 10 may include a device or garment, such as a snug fitting shirt, which is worn on the wearer's leg, arm, chest, or wrist.

In addition, it is defined that a part of the wearable measurement apparatus 10 that is in contact with the body part is a lower part and a part in which a display 113 is disposed is an upper part.

Figure 2:
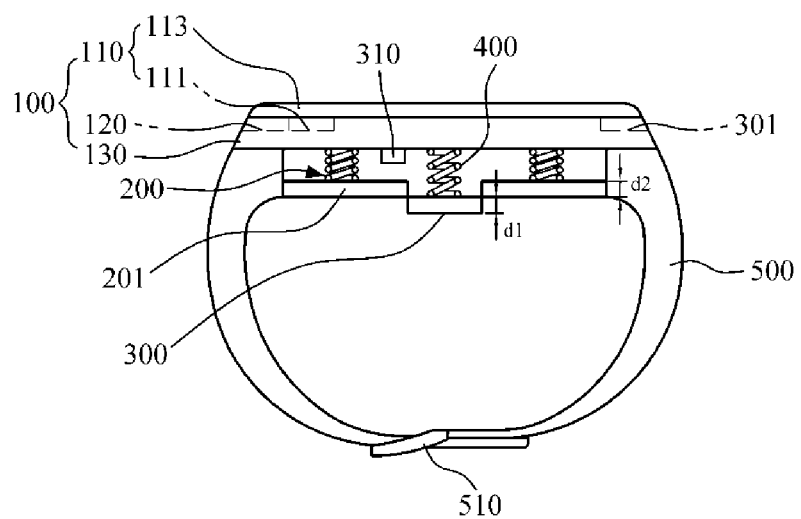
FIG. 2 is a cross-sectional view taken along line I-I' of FIG. 1.

FIG. 1 is a perspective view of the wearable measurement apparatus 10 according to an exemplary embodiment. FIG. 2 is a cross-sectional view taken along line I-I' of FIG. 1.

Referring to FIGS. 1 and 2, the wearable measurement apparatus 10 includes a main body 100, a main-body elastic part 200, a biometric signal sensor 300, and a sensor elastic part 400.

The main-body elastic part 200 is connected to a lower portion of the main body 100 and elastically supports the main body 100 against the wearer's body 20. The biometric signal sensor 300 is disposed to be spaced apart from the main-body elastic part 200 and detects a biometric signal from the wearer's body part 20. The sensor elastic part 400 is interposed between the main body 100 and the biometric signal sensor 300 to form a step difference between the bottom surface of the biometric signal sensor and the bottom surface of the main-body elastic part 200, and the sensor elastic part 400 elastically supports the biometric signal sensor 300 against the main body 100. The wearable measurement apparatus 10 may further include a strap 500. The strap 500 extends from the main body 100. The strap 500 allows the main body 100 to be fixed on the wearer's body part 20, thereby enabling the wearer to put the main body 100 on the body part 20.

The main-body elastic part 200 is resilient having a predetermined modulus of elasticity so that when an external force is exerted on the main-body elastic part 200, the main-body elastic part 200 is deformed, and, when the exerted force is removed, is restored back to the original shape.

In this case, the main-body elastic part 200 may have a greater modulus of elasticity than that of the sensor elastic part 400. Accordingly, when the main-body elastic part 200 is compressed and deformed as an external force is applied, a degree of elastic deformation of the main-body elastic part 200 is smaller than that of the sensor elastic part 400, and hence the degree of compression thereof is also smaller than that of the sensor elastic part 400. However, the modulus of elasticity of the main-body elastic part 200 is not infinite, and the main-body elastic part 200 may have greater elasticity and restoration than those of a rigid structure generally used.

In addition, the modulus of elasticity of the main-body elastic part 200 may vary depending on the purpose of use and a specific modulus of elasticity that is used to provide a comfortable wearing sensation may be selected.

The main-body elastic part 200 in accordance with one aspect is disposed on each side of the biometric signal sensor 300 and supports the main body 100 against the wearer's body part 20. In this case, the position of the main-body elastic part 200 is not limited to the above example, and may be disposed at any position of the lower surface of the main body 100 at which it is possible to support the main body 100 against the wearer's body part 20. Although in this example, it is described that the main-body elastic part 200 is divided into two sections between which the biometric signal sensor 300 is interposed and that are disposed along the circumference of the wearer's wrist, the main-body elastic part 200 may be disposed at a distance from the edge of the biometric signal sensor 300.

The main-body elastic part 200 may include a spring. The main-body elastic part 200 may be, for example, a coil spring, or may be a spiral spring, a leaf spring, or a disk spring for minimizing the thickness thereof.

However, the main-body elastic part 200 are not limited to the above examples and may include any elastic members, such as Ultem, Polhesterimids (PEI), high elastic steel, TR-90, and the like, which can have an modulus of elasticity.

The main-body elastic part 200 may further include a support member 201 disposed on a lower portion of the main-body elastic part 200. The support member 201 may include any members that make direct contact with the wearer's body part 20 and can improve the wearing sensation.

The support member 201 is divided into two sections between which the biometric signal sensor 300 is interposed and that are disposed along the circumference of the wearer's wrist, or the main-body elastic part 200 may be disposed at a distance from the edge of the biometric signal sensor 300.

The biometric signal sensor 300 may be spaced apart from the main-body elastic part 200 and be disposed on a lower portion of the main body 100. The biometric signal sensor 300 is disposed in the central opening of a housing 130 and goes into and out of the housing in a vertical direction. The biometric signal sensor 300 may be connected with the sensor elastic part 400 connected at the lower portion of the main body 100. In addition, the bottom surface of the biometric signal sensor 300 has a step difference with the bottom surface of the main-body elastic part 200.

According to an exemplary embodiment, without an external force applied onto the top portion of the biometric signal sensor 300, the bottom surface of the biometric signal sensor 300 is positioned lower than the bottom surface of the main-body elastic part 200. That is, with respect to the wearer's body part 20 that the biometric signal sensor 300 is in contact with, the bottom surface of the biometric signal sensor 300 is lower than the bottom surface of the main-body elastic part 200.

Therefore, when the wearer wears the wearable measurement apparatus 10, the wearer's body part 20 may make sequential contact with the biometric signal sensor 300 and the main-body elastic part 200. That is, when the body part 20 of the wearer is pressurized to the main body 100 when the wearer is wearing the wearable measurement apparatus 10, the wearer's body part 20 is first in contact with the biometric signal sensor 300, and then the sensor elastic part 400 that supports the biometric signal sensor 300 is compressed and deformed, so that the body part 20 is substantially in contact with the main-body elastic part 200.

The biometric signal sensor 300 in accordance with one aspect may include an optical sensor. The optical sensor may include a light source that generates light used to detect a biometric signal of a body part of interest and a photodetector that detects the intensity of the light reflected from the body part of interest.

For example, the light source may include a light emitting diode (LED) or a laser diode.

The photodetector may include, for example, a photodiode, a photo transistor (PTr), or a charge-coupled device (CCD). The photodetector may sense an optical signal scattered or reflected from an object of interest and detect laser speckle produced by scattering of the laser light that has been emitted to the object of interest.

However, the biometric signal sensor 300 is not limited to the above examples and may include an electromyography (EMG) sensor, an electrodermal activity sensor, a skin temperature measuring instrument, a blood volume pulse measuring instrument, an electrocardiogram (ECG) sensor, a respiration sensor, a blood pressure measuring instrument, and a heart rate measuring instrument, or other combinations thereof.

The EMG sensor senses the action potential of muscles. The electrodermal activity sensor senses the conductivity of skin. The skin temperature measuring instrument may include a sensor for measuring the temperature of the skin surface. The blood volume measuring instrument is a device that measures the amount of blood running in the vessel. The ECG sensor detects the potential associated with the heartbeat on the body surface. The respiration sensor measures the breathing frequency and relative depth of breathing. The heart rate measuring instrument measures the number of heartbeats per unit time.

The example described above assumes that there is provided one biometric signal sensor 300 in accordance with one aspect to detect a biometric data signal, but the present disclosure is not limited thereto. For example, a biometric data signal of the wearer may be detected through two detections sensors ("two channels"), and the number and shape of the biometric signal sensors 300 may vary or be modified.

In addition, an object of interest of the biometric signal sensor 300 may be a body part that is a target object near which the biometric signals sensor can be located. For example, the human body part at which the pulse wave can be easily measured through photolethysmography (PPG) may be an area near the radial artery of the surface of the wrist, and, not limited thereto, distal areas of the body with a high density of blood vessels, such as fingers, toes, or earlobes.

Moreover, the biometric signal sensor 300 detects the biometric data of the wearer and provides relevant information to the wearable measurement apparatus 10. For example, the biometric signal sensor 300 may emit light onto the body part 20 of the wearer and receive light reflected from the body part 20 so that the blood flow change of the radial artery due to the contraction and relaxation of the heart, i.e., the change in the volume of blood vessels can be measured using the light.

The sensor elastic part 400 in accordance with one aspect may be formed such that the bottom surface of the biometric signal sensor 300 is lower than the bottom surface of the main-body elastic part 200. In other words, the sensor elastic part 400 may be formed such that the bottom surface of the biometric signal sensor 300 is positioned lower than the bottom surface of the main-body elastic part 200 with respect to the wearer's body part 20 that the wearable measurement apparatus 10 is in contact with.

Accordingly, when the wearer is wearing the wearable measurement apparatus 10, the biometric signal sensor 300 and then the main-body elastic part 200 can be sequentially in contact with the wearer's body part 20.

The sensor elastic part 400 is resilient having a predetermined modulus of elasticity so that the sensor elastic part 400 is deformed when an external force is exerted thereon, and when the exerted force is removed, it is restored back to the original shape. Hence, the wearable measurement apparatus 10 may measure the wearer's biometric data while being in contact with the wearer's body part 20, and the wearer can perform various physical activities with the wearable measurement apparatus 10 on the body part 20.

However, the sensor elastic part 400 may have a smaller modulus of elasticity than that of the main-body elastic part 200. That is, when an external force is applied, a degree of elastic deformation of the sensor elastic part 400 is greater than that of the main-body elastic part 200 and, in turn, is compressed more than the main-body elastic part 200. Accordingly, when the wearable measurement apparatus 10 measures the biometric signal of the wearer, it is possible to maintain an adequate contact sensation on the measured body part while minimizing a pressing sensation on the other body parts than the measured part, and minimize the change due to disturbance.

The sensor elastic part 400 may include a spring. The sensor elastic part 400 may be, for example, a coil spring, or may be a spiral spring, a leaf spring, or a disk spring for minimizing the thickness.

However, the sensor elastic part 400 are not limited to the above examples and may include any elastic members, such as Ultem, PEI, high elastic steel, TR-90, and the like, which can have an modulus of elasticity.

The strap 500 may be flexibly formed to encircle the wearer's body part 20, for example, the wrist. The strap 500 wrapping around the wearer's wrist may be tightened or loosened, thereby pressurizing or depressurizing the wearer's body part 20. When the biometric signal sensor 300 is not in sufficient contact with the wearer's body part 20 and hence impossible to measure a biometric signal, the wearer may further tighten the strap 500 so that the biometric signal sensor 300 is in close contact with the body part 20. The strap 500 may be connected to each side of the main body 100 or to the bottom surface of the main body 100. According to one aspect, the strap 500 includes two strap members and the strap members are engaged or disengaged with each other by an engager 510. It is illustrated that the engager 510 includes a buckle, but the engager 510 may include Velcro or the like.

The strap 500 may be formed as a closed loop without using a separate engager. In addition, the strap 500 may be formed of elastic mesh/fabric and may be formed with a multi-band or the like.

The strap 500 may further include an ECG sensor that measures the electroactivity of the wearer and may further include a thermometer that measures a body temperature or a body temperature gradient.

So far, the configuration of the wearable measurement apparatus 10 is described above. Hereinafter, the operation of the wearable measurement apparatus 10 in accordance with an exemplary embodiment will be described.

Figure 3:
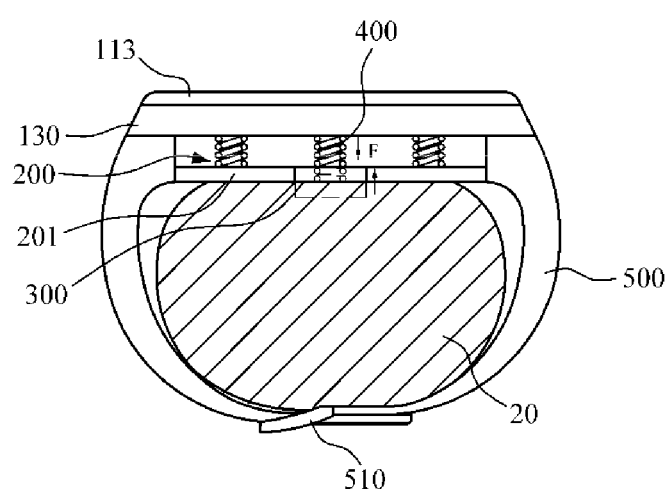
FIG. 3 is a diagram illustrating an operation of the wearable measurement apparatus of FIGS. 1 and 2.

FIG. 3 is a diagram illustrating the operation of the wearable measurement apparatus 10 of FIGS. 1 and 2.

Referring to FIG. 3, when a wearer puts on the wearable measurement apparatus 10, the wearer's body part 20 is in contact with the biometric signal sensor 300. Then, when the biometric signal sensor 300 is pressurized by the wearer's body part 20, for example, when the wearer tightens the strap 500 of the wearable measurement apparatus 10, the sensor elastic part 400 that elastically supports the biometric signal sensor 300 may be compressed. Accordingly, the biometric signal sensor 300 makes close contact with the body part 20 due to the elasticity of the sensor elastic part 400.

When artery information of the wearer is to be detected, the bottom surface of the biometric signal sensor 300 is placed at a position corresponding to the artery of the wearer's wrist and detects blood pressure information of the artery while in close contact with the skin above the artery.

For example, in the case in which the biometric signal sensor 300 includes a light source and a photodetector, the light source may emit light onto the wearer's body part 20, and the photodetector may receive the light reflected from the body part 20, so that the blood flow change of the radial artery due to the contraction and relaxation of the heart, i.e., the change in the volume of blood vessels can be measured using the light.

In this case, when it is assumed that a range (from the bottom surface of the biometric signal sensor 300 to the bottom surface of the main-body elastic part 200) in which the sensor elastic part 400 is pressurized is d1, the displacement of the sensor elastic part 400 within d1 is determined by an external force and the modulus of elasticity of the sensor elastic part 400, and the elastic force or the restoring force (i.e., F) of the sensor elastic part 400 may be imposed on the body part 20. Thus, the biometric signal sensor 300 can remain in close contact with the wearer's body part 20, so that it is possible to improve the accuracy and quality of the biometric signal sensor 300.

When a range of displacement in which the main-body elastic part 200 is pressurized is d2, the displacement of the main-body elastic part 200 may be determined by a synthesized modulus of elasticity of the sensor elastic part 400 and the main-body elastic part 200. Thus, the change of the displacement within d2 may be relatively small, compared to that of the displacement within d1.

When the main-body elastic part 200 is compressed within d2, comfortable wearing sensation may be provided to the wearer.

Referring back to FIGS. 1 and 2, the main-body 100 in accordance with one aspect includes a base portion 110, a battery 120, and a housing 130.

The base portion 110 may include a controller 111 that analyzes the biometric signal of the wearer and a display 113 that displays an analyzed biometric signal. The base portion 110 may execute various instructions input through an input/output device, such as a graphic user interface (GUI), or process collected measurement values and display the result.

The base portion 110 may wirelessly communicate with a connected external device. For example, the base portion 110 may wirelessly communicate with wireless accessible devices, such as a smartphone, a tablet PC, or other calculation devices.

In addition, the base portion 110 may be formed to be flexible. In this case, the base portion 110 may be bent along the curve or motion of the wearer's body part 20 on which the wearable measurement apparatus 10 is put, and hence the reliability of wearing can be improved. Accordingly, it is possible to minimize uncomfortable feeling that the wearer may experience when performing activities with the wearable measurement apparatus 10 on his/her body part.

The controller 111 may include a processor, a memory, an input/output device, and a communication interface and may be connected with the biometric signal sensor 300. The controller 111 may generate data about the wearer's condition or the wearer's physical activities from the values detected by the biometric signal sensor 300 and analyze the biometric signal or the change in the biometric signal according to the physical activities.

The controller 111 may analyze a pulse-wave signal detected by the biometric signal sensor 300. The controller 111 may obtain the biometric signal by analyzing laser speckle fluctuation that corresponds to change in variable volume of laser speckle corresponding to the volume change of the blood vessel, e.g., the radial artery, of an object of interest. In this case, the obtained biometric signal may be a PPG signal that is converted based on a correlation between the analyzed speckle fluctuation and the volume change. The controller 111 may analyze various parameters included in the PPG pulse-wave signal by analyzing a wave characteristic of the PPG pulse-wave signal.

For example, the controller 111 may compute a delay time between pulse-wave signals and calculate a pulse transit time (PTT). During this process, the controller 111 may use various digital signal processing algorithms, such as a noise reduction algorithm, a differential signal extraction algorithm, etc.

The controller 111 may analyze various biometric data using the pulse wave signal analysis result as an index. A biometric data analyzer of the controller 111 may analyze biometric data using a predetermined algorithm for calculating various biometric data from the PPT analyzed by a pulse-wave analyzer. For example, the biometric data analyzer may estimate elasticity of blood vessels, a blood flow speed, stiffness of artery, a systolic blood pressure, a diastolic blood pressure, or the like In addition, the controller 111 may determine whether the analyzed biometric signal is within a normal range. For example, when a pressing force exerted by the biometric signal sensor 300 on the body is high, the contraction/relaxation of blood vessels of the wearer are restricted and hence it is not possible to measure the biometric signal, whereas when a pressing force exerted by the biometric signal sensor 300 on the body is substantially small, it is not possible to measure the contraction/relaxation of blood vessels of the wearer. Thus, it is determined whether the biometric signal is within the predetermined normal range. The controller 111 may measure the pressing force through a compression sensor 310, which will be described below, then analyze a biometric signal, and, if the pressing force is too high to measure the biometric signal, advise the wearer to reduce the pressing force.

On the contrary, when the pressing force is too small to measure the biometric signal, the controller 111 may advise the wearer to increase the pressing force.

The processor may include a single processor having at least one core or a multi-processor having at least one core. The processor may be implemented to accept, receive, convert, and process an audio frequency instruction from the wearer in cooperation with the input/output device.

The processor may execute instructions or various applications of an operating system (OS). The processor may control an interaction of instruction between the elements of the wearable measurement apparatus 10 and communications of the input/output device.

The memory may store a program for processing and control of the processor and store input/output data. The memory may include any one or any combination of a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like.

The input/output device may be a set of elements that receive information from an external source or the wearer and output corresponding information. For example, the input/output device may include a microphone, a camera and a speaker, and may further include an audio chip, a display controller, and a touchscreen controller.

The communication interface may include a configuration for supporting one-way or two-way radio communications and may remotely receive or output data. The communication interface may include a wireless network interface for a network of a wired interface or multiple interfaces.

The communication interface may support a radio-frequency communication and include Bluetooth low energy (BLE), wireless local area network (WLAN), WiMAX, manual radio frequency identification (RFID), and network adaptors and modems. In addition, the communication interface may include a wide area network (WAN) interface, Wi-Fi, WPAN, multi-hop network, a cellular network (e.g., 3G, 4G, 5G, or long term evolution (LTE)), or the like. Further, the communication interface may include ultrawide band (UWB), infrared, etc. However, the communication interface is not limited to the above examples and may include other types of communications, for example, a serial communication and/or a universal serial bus (USB) communication, than the radio communications.

The display 113 may present information to the wearer and include a touchscreen or a controllable gesture. The display 113 may include, for example, an organic light emitting diode (OLED) display or a thin-film transistor liquid crystal display (TFT LCD). In another example, the display 113 may be formed to be 3-dimensional (3D) or flexible, or may be disposed in a flat or curved manner. The curved manner indicates that the display 113 has a curvature relative to the body part on which the wearable measurement apparatus 10 is put.

The display 113 may be integrated with, for example, the controller 111. In another example, the display 113 may be provided outside of the controller 111.

The battery 120 may supply power to the wearable measurement apparatus 10. For example, the battery 120 may include a rechargeable battery. The rechargeable battery is a battery that can be charged after being discharged. In the case in which the housing 130 has an input/output port, such as a USB port, the battery 120 may be charged by an external AC/DC power supply connected with the input/output port. The battery 120 may be charged using a wireless charging mechanism or solar cells. The battery 120 may be built in the strap 500. The battery 120 may be configured to be detachably coupled to the housing 130.

The housing 130 may be configured to surround the base portion 110 and the battery 120. The housing 130 may be made of an elastic material having a sealing capability, such as rubber, silicon group material or an elastomer, so that the housing 130 attached on the wearer's body part can be flexibly changed in shape according to the movement of the wearer.

In addition, the housing 130 may be made of a nonconductive or insulating material, for example, an insulating resin or the like. Moreover, the housing 130 in accordance with one aspect may be formed in rectangular shape or various shapes according to the connection state of the base portion 110, which will be described below.

The housing 130 may be vacuum-formed such that the housing 130 is sealed with the base portion 110 and the battery 120 mounted therein, so that the housing 130, the base portion 110, and the battery 120 are formed as one piece.

The housing 130 in accordance with one aspect may have an opening on the lower portion through which the biometric signal sensor 300 can pass in a vertical direction.

The wearable measurement apparatus 10 may further include a state information sensor 301. The state information sensor 301 may include, for example, an acceleration sensor. The acceleration sensor may detect X-axis, Y-axis, and Z-axis data of the body according to an activity state of the wearer and measure the wearer's posture (e.g., sitting, standing, lying down) or rapid body change due to a physical activity, so that a resulting value to be acquired can be modified by applying these measurement data.

In addition, the state information sensor 301 may include, for another example, a temperature sensor. The temperature sensor may detect the body temperature of the wearer or a temperature of the surroundings and measure the body temperature change of the wearer and the surrounding environment of the wearer, so that a resulting value to be acquired can be modified by applying these measurement data.

Moreover, the state information sensor 301 may include, for example, a humidity sensor. The humidity sensor may detect the wearer's condition based on sweat produced on the wearer's body 20 or the humidity of the surrounding environment of the wearer and measure a surrounding environment state (e.g., whether the wearer is exercising, fomenting, or in shower) of the wearer based on the detected values, so that a resulting value to be acquired can be modified by applying the measurement data.

Further, the state information sensor 301 may include, for example, a sound detection sensor. The sound detection senor may detect sound produced during food intake or sound produced from the outside and may determine whether the wearer has not had a meal or already had a meal, so that a resulting value to be acquired can be modified by applying the detection result.

The state information sensor 301 as described above may be provided in various ways, and one or multiple state information sensors 301 may be mounted. When a plurality of detection sensors is provided, it is possible to combine data according to the above-described detection values and detect the state of the wearer. For example, in the case in which the acceleration sensor and the temperature-humidity sensor are mounted together, the acceleration sensor may detects information related to the posture or motion of the wearer, and at the same time, the temperature-humidity sensor may detect change in temperature or change in humidity, such as sweat, so that it is possible to accurately estimate that the wearer is exercising and a resulting value can be determined by reflecting a corresponding change in the biometric signal. That is, it is possible to detect the wearer's state in which the biometric signal is changed due to the exercise the wearer is performing, and also it is possible to detect accurate data about an exercise state of the wearer.

The state information sensor may include a microelectromechanical systems (MEMS) accelerometer. The MEMS accelerometer may be used to measure information about a position, a motion, a tilt, a shock, a vibration, and the like, which is to be used by the processor. In addition, the state information sensor may include a biological sensor (pulse oximeter, temperature, blood pressure, body fat), a proximity detector used to detect the proximity of objects, and an environmental sensor (temperature, humidity, illumination, pressure, altitude, bearings).

The wearable measurement apparatus 10 in accordance with one aspect may further include the compression sensor 310. The compression sensor 310 may measure a pressing force exerted by the biometric signal sensor 300 on the wearer's body part 20 when the wearable measurement apparatus 10 is in close contact with the wearer's body part 20. The measured value of the pressing force is delivered to the controller 111, so that the controller 111 can determine the most suitable pressing force for the wearer when measuring a biometric signal.

In addition, the compression sensor 310 may include a force sensor to directly measure the pressing force, or may include a displacement sensor. The displacement sensor may measure a displacement of the biometric signal sensor 300 or the sensor elastic part 400. The displacement sensor may deliver a measured displacement value to the controller 111. The displacement sensor may include, for example, a resistive-type strain gauge, an optical-type distance sensor, and a piezoelectric sensor. However, the displacement sensor is not limited to the above examples and may include any type of displacement sensor capable of measuring the displacement of the sensor elastic part 400.

The pressing force measured by the compression sensor 310 may be presented by the display 113. In this case, the display 113 may display the pressing force in various ways, for example, as a grade or a numerical value.

Figure 4:
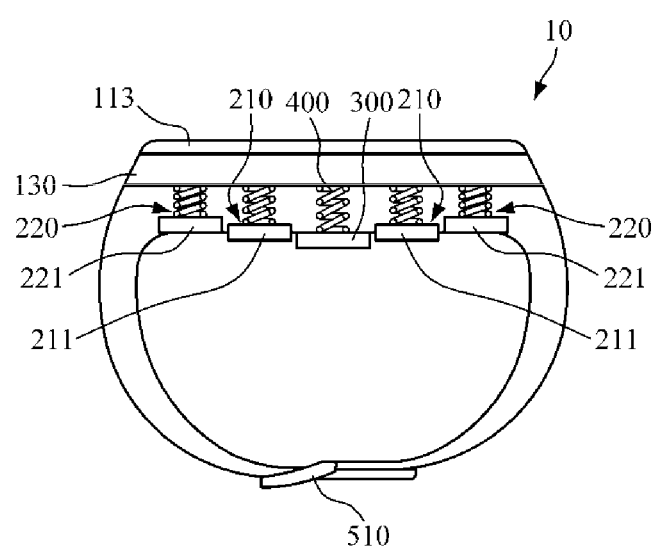
FIG. 4 is a cross-sectional view of a wearable measurement apparatus including a main-body elastic part, according to another exemplary embodiment.

FIG. 4 is a cross-sectional view of the wearable measurement apparatus 10 including a main-body elastic part, according to another exemplary embodiment. What has been described above will be omitted.

Referring to FIG. 4, the main-body elastic part 200 in accordance with another exemplary embodiment includes a first main-body elastic part 210 and a second main-body elastic part 220. A bottom surface of the first main-body elastic part 210 and a bottom surface of the second main-body elastic part 220 may be at different heights.

For example, the bottom surface of the first main-body elastic part 210 is at a lower height than the bottom surface of the second main-body elastic part 220, but is at a higher height than a bottom surface of the biometric signal sensor 300. In addition, the first main-body elastic part 210 in accordance with one aspect may be disposed closer to the biometric signal sensor 300 than the second main-body elastic part 220.

In this case, the wearer's body part 20 may be in sequential contact with the biometric signal sensor 300, the first main-body elastic part 210, and the second main-body elastic part 220.

When the wearer puts on the wearable measurement apparatus 10, the wearer's body part 20 may first make contact with the biometric signal sensor 300. Then, as the wearable measurement apparatus 10 is more pressurized by the wearer's body part 20, the sensor elastic part 400 that elastically supports the biometric signal sensor 300 may be compressed. Accordingly, the wearer's body part 20 becomes in contact with the first main-body elastic part 210, as well as the biometric signal sensor 300.

In this case, when the first main-body elastic part 210 is more pressurized, the wearer's body part 20 may be in contact with the sensor elastic part 400, the first main-body elastic part 210, and the second main-body elastic part 220.

As described above, because a synthesized modulus of elasticity differs among the cases in which only the sensor elastic part 400 is pressurized, in which both the sensor elastic part 400 and the first main-body elastic part 210 are pressurized, and in which the sensor elastic part 400, the first main-body elastic part 210 and the second main-body elastic part 220 are all pressurized, a supporting force for support for the wearer's body part 20 and the overall synthesized resilient restoration may vary according to the degree of compression. Accordingly, a contact force of the biometric signal sensor 300 can be variously changed, so that the controller 111 can easily measure a suitable contact force for the wearer in measuring the biometric signal. Consequently, the controller 111 can advise the wearer of the most suitable contact force in measuring the biometric signal.

The first main-body elastic part 210 and the second main-body elastic part 220 may have the same modulus of elasticity, or may have different moduli of elasticity. On one lower end of the first main-body elastic part 210, a support member 211 may be further disposed to improve the wearing sensation, and also on a lower end of the second main-body elastic part 220, a support member 221 may be disposed to improve the wearing sensation.

In addition a third main-body elastic part that is disposed on one side of either the first main-body elastic part 210 or the second main-body elastic part 220 may be further provided.

Figure 5:
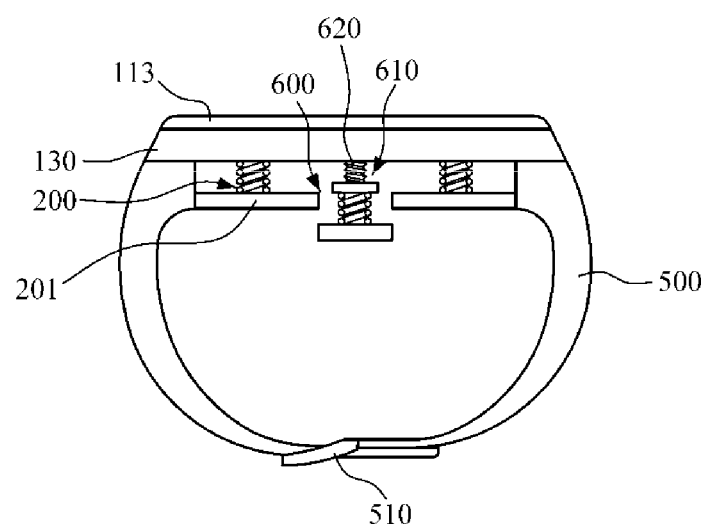
FIG. 5 is a cross-sectional view of a wearable measurement apparatus including a step-difference control portion, according to another exemplary embodiment.

FIG. 5 is a cross-sectional view of a wearable measurement apparatus including a step-difference control portion 600, according to another exemplary embodiment.

Referring to FIG. 5, the wearable measurement apparatus in accordance with one aspect further includes the step-difference control portion 600 that is interposed between the main body 100 and the sensor elastic part 400.

The step-difference control portion 600 may adjust a step difference between the bottom surface of the biometric signal sensor 300 and the bottom surface of the main-body elastic part 200. For example, the step-difference control portion 600 may increase the step difference between the bottom surface of the biometric signal sensor 300 and the bottom surface of the main-body elastic part 200 to increase the pressing force exerted by the biometric signal sensor 300 on the body part 20. On the contrary, the step-difference control portion 600 may decrease the step difference between the bottom surface of the biometric signal sensor 300 and the bottom surface of the main-body elastic part 200 to reduce the pressing force exerted by the biometric signal sensor 300 on the body part 20.

The step-difference control portion 600 may be manually controlled by the wearer or automatically controlled by the controller 111.

The step-difference control portion 600 may include a lifting block 610 and a control instrument 620 for lifting up and down the lifting block 610, wherein the lifting block 610 is coupled to the sensor elastic part 400 and drives the sensor elastic part 400 and the biometric signal sensor 300 up and down.

The lifting block 610 may adjust the height of the biometric signal sensor 300 by moving up or down, and accordingly, the step difference between the bottom surface of the main-body elastic part 200 and the bottom surface of the biometric signal sensor 300 can be adjusted. The up and down movements of the lifting block 610 may be guided by a lifting guide, without rotary movement.

The control instrument 620 may drive the lifting block 610 in a vertical direction. The control adjustment 610 may include, for example, a screw coupled to the lifting block 610 and a rotary lever used by the wearer to rotate the screw. In another example, the screw may be automatically rotated by a rotary motor. In another example, the control instrument 620 may include a linear actuator to lift up and down the lifting block 610.

Figure 6:
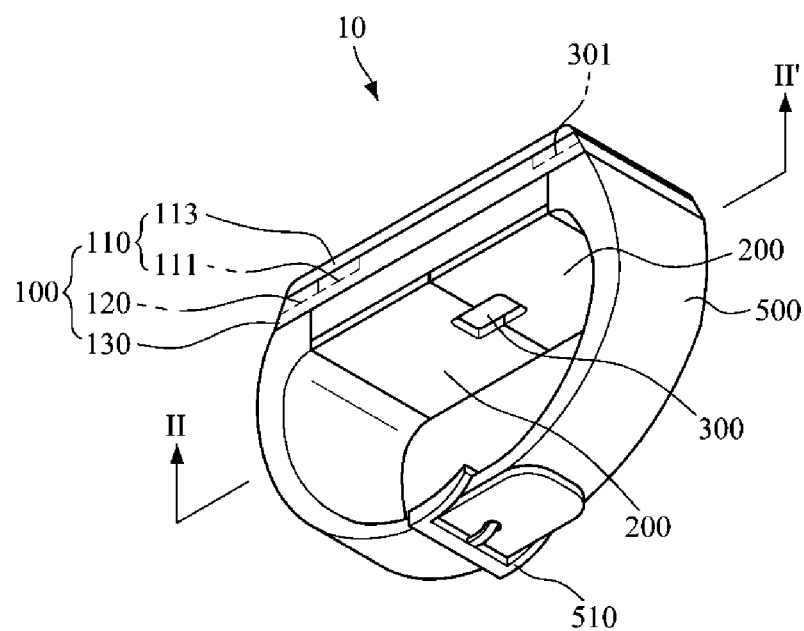
FIG. 6 is a perspective view of a wearable measurement apparatus according to another exemplary embodiment.
Figure 7:
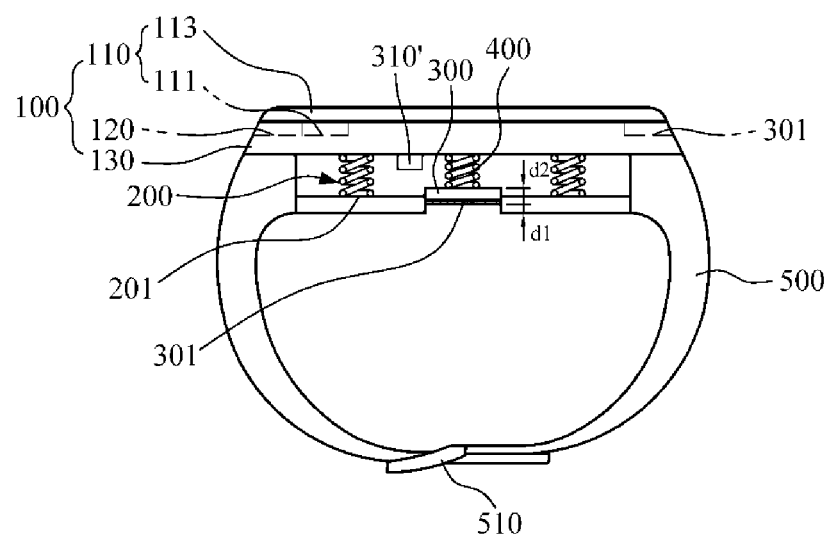
FIG. 7 is a cross-sectional view taken along line II-II' of FIG. 6.

FIG. 6 is a perspective view of the wearable measurement apparatus 10 according to another exemplary embodiment, and FIG. 7 is a cross-sectional view taken along line II-II' of FIG. 6.

The configuration of the wearable measurement apparatus 10 illustrated in FIGS. 6 and 7 is only an example and may be modified to a different shape.

Referring to FIGS. 6 and 7, as is similar to the above-described exemplary embodiments, the biometric signal sensor 300 is disposed to be spaced apart from the main-body elastic part 200 and detects a biometric signal from the wearer's body part 20. The biometric signal sensor 300 may be connected to the sensor elastic part 400 that is connected to a lower portion of the main body 100.

In this case, the bottom surface of the biometric signal sensor 300 may be positioned higher than the bottom surface of the main-body elastic part 200. That is, That is, with respect to the wearer's body part 20 that the wearable measurement apparatus 10 is in contact with, the bottom surface of the biometric signal sensor 300 is higher than the bottom surface of the main-body elastic part 200.

Therefore, when the wearer puts on the wearable measurement apparatus 10, the wearer's body part 20 may make sequential contact with the main-body elastic part 200 and the biometric signal sensor 300. That is, when the wearer's body part 20 pressurizes the main body 100 of the wearable measurement apparatus 10, the wearer's body part 20 may be first in contact with the main-body elastic part 200 and as the main-body part 200 is pressurized, the body part 20 may be substantially in contact with the biometric signal sensor 300.

In this case, the biometric signal sensor 300 may include an adhesive member 310 disposed on the bottom surface thereof. The adhesive member 310 may allow the biometric signal sensor 300 to be attached onto the wearer's body. The adhesive member 310 may include, for example, a silicon adhesive or a biomimetic adhesive, but is not limited thereto, and may include any material that can be attached to the wearer's body part 20. In another example, the adhesive member may include sucker.

The wearable measurement apparatus 10 in accordance with one aspect may further include an adsorption sensor 310'. The adsorption sensor 310' may be used to measure an adsorption force imposed by the biometric signal sensor 300 on the wearer's body part 20 when the wearable measurement device 10 is in close contact with the wearer's body part 20. The measured value of adsorption force is delivered to the controller 111, and the controller may determine the most suitable absorption force for the wearer in measuring a biometric signal.

The adsorption sensor 310' may include a displacement sensor to measure a displacement of the biometric signal sensor 300 or the sensor elastic part 400. The displacement sensor may deliver a measured displacement value to the controller 111. The controller 111 calculates the adsorption force based on the displacement measured by the displacement sensor and a modulus of elasticity. The adsorption force measured by the adsorption sensor 310' may be presented by the display 113. The display 113 may display the adsorption force in various ways, for example, as a grade or a numerical value.

As is similar to the exemplary embodiments described above, a step-difference control portion 600 may be interposed between the main body 100 and the sensor elastic part 400 and may adjust the step difference between the bottom surface of the biometric signal sensor 300 and the bottom surface of the main-body elastic part 200.

So far, the configuration of the wearable measurement apparatus 10 in accordance with another exemplary embodiment has been described. Hereinafter, the operation of the wearable measurement apparatus 10 in accordance with another exemplary embodiment will be described.

Figure 8:
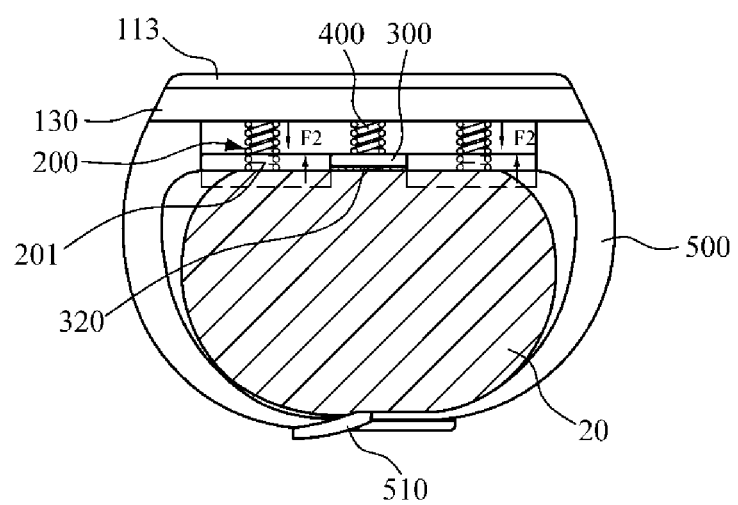
FIGS. 8 and 9 are diagrams illustrating an operation of the wearable measurement apparatus of FIG. 7.
Figure 9:
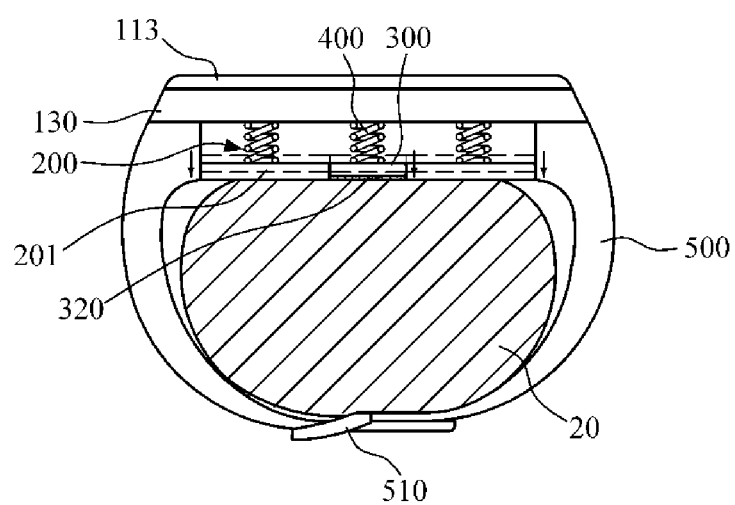

FIGS. 8 and 9 are diagrams illustrating an operation of the wearable measurement apparatus 10 of FIG. 7.

Referring to FIG. 8, when a wearer puts on the wearable measurement apparatus 10, the wearer's body part 20 may be first in contact with the main-body elastic part 200. Then, when the main-body elastic part 200 is pressurized by the wearer's body part 20, for example, when the wearer tightens the strap 500 of the wearable measurement apparatus 10, the main-body elastic part that supports the main body 100 may be compressed.

In this case, when it is assumed that a range (from the bottom surface of the main-body elastic part 200 to the bottom surface of the biometric signal sensor) in which the main-body elastic part 200 is pressurized is d1, the displacement of the main-body elastic part 200 within d1 is determined by an external force (i.e., F2) and the modulus of elasticity of the main-body elastic part 200.

Then, when the biometric signal sensor 300 is in contact with the wearer's body part 20 as the main-body elastic part 200 is further pressurized by the wearer's body part 20, an adhesive member 320 disposed on one surface of the biometric signal sensor 300 may be adhered to and in contact with the wearer's body part 20. In this case, for example, the adhesive member 320 may be attached on each side of the artery of the wearer's wrist, and the biometric signal sensor 300 that is in contact with the artery of the wearer's wrist may measure a biometric signal.

Referring to FIG. 9, when the external force is removed and, in turn, the main-body elastic part 200 is restored to the original state, the sensor elastic part 400 may be stretched because the adhesive member 320 of the biometric signal sensor 300 is attached to the body part via the adhesive member 320. In this case, the wearer's body part 20 may experience negative pressure from the sensor.

When the wearer's body part 20 is applied negative pressure from the sensor, the wearer may be provided with a comfortable sensation of wearing the wearable measurement device 10, so that the wearer can measure a biometric signal without experiencing a pressing force.

The biometric data measured by the wearable measurement apparatus may be delivered to and used by a computer system that provides health care information to the wearer via a wireless communication. The computer system may include clients and servers. The clients and the servers are located at distance from each other and may interact with each other via a communication network. Values of computer programs that run on the respective computers and are in client-server relationship may affect the relationship between the clients and servers. Various cloud-based platforms and/or other database platforms may transmit and receive data to and from the controller 111. Such an implementation may be realized as a structure for multi-modal interaction. The structure may be employed as artificial intelligence (AI) layers between wearable devices and large scale Cloud, websites, online services and applications of other devices. In addition, the above structure may convert input data from the controller 111 and provide a service used to advise the wearer or the health care expert according to change in conditions. Further, the structure may facilitate the interaction between the wearable device and information (e.g., social media, sports, music, movie, emails, text messages, hospital, and prescription).

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable measurement apparatus comprising:
   a main body comprising a display;
   a support member configured to contact a body part of a user;
   a main-body elastic part interposed between a bottom surface of the main body and the support member, and configured to elastically support the support member against the main body;
   a biometric signal sensor disposed apart from the main-body elastic part, and configured to detect a biometric signal from the body part;
   a sensor elastic part directly contacting the bottom surface of the main body and directly contacting a top surface of the biometric signal sensor, and configured to:
      form a step difference between a bottom surface of the biometric signal sensor and a bottom surface of the support member; and
      elastically support the biometric signal sensor against the main body; and
   a lifting block having a bottom surface coupled to a top surface of the sensor elastic part, and configured to move up and down the sensor elastic part and the biometric signal sensor in order to adjust the step difference.

2. The wearable measurement apparatus of claim 1, wherein the sensor elastic part is disposed such that the bottom surface of the biometric signal sensor is positioned lower than the bottom surface of the support member.

3. The wearable measurement apparatus of claim 2, wherein the main-body elastic part has a modulus of elasticity greater than a modulus of elasticity of the sensor elastic part.

4. The wearable measurement apparatus of claim 2, further comprising a strap connected to the main body, and configured to allow the wearable measurement apparatus to be disposed on the body part.

5. The wearable measurement apparatus of claim 2, further comprising a compression sensor configured to measure a pressing force that is exerted on the body part when the biometric signal sensor is in contact with the body part.

6. The wearable measurement apparatus of claim 5, further comprising a controller,
   wherein the compression sensor comprises a displacement sensor configured to measure a displacement of the sensor elastic part and a displacement of the main-body elastic part, and
   the controller is configured to determine the pressing force, based on the measured displacement of the sensor elastic part, the measured displacement of the main-body elastic part, a modulus of elasticity of the sensor elastic part, and a modulus of elasticity of the main-body elastic part.

7. The wearable measurement apparatus of claim 5, wherein the display is configured to display the pressing force.

8. The wearable measurement apparatus of claim 2, further comprising a controller configured to determine whether the biometric signal is within a normal range.

9. The wearable measurement apparatus of claim 2, further comprising a step-difference control portion configured to adjust the step difference between the bottom surface of the biometric signal sensor and the bottom surface of the support member.

10. The wearable measurement apparatus of claim 2, wherein the main-body elastic part comprises a first main-body elastic part and a second main-body elastic part,
    the first main-body elastic part comprises a first spring, and the second main-body elastic part comprises a second spring, and
    a bottom surface of the first main-body elastic part and a bottom surface of the second main-body elastic part are at different heights.

11. The wearable measurement apparatus of claim 1, wherein the sensor elastic part is formed such that the bottom surface of the biometric signal sensor is positioned higher than the bottom surface of the support member.

12. The wearable measurement apparatus of claim 11, further comprising an adhesive member disposed on the bottom surface of the biometric signal sensor, and configured to attach the biometric signal sensor to the body part.

13. The wearable measurement apparatus of claim 11, wherein the main-body elastic part has a modulus of elasticity greater than a modulus of elasticity of the sensor elastic part.

14. The wearable measurement apparatus of claim 11, further comprising a strap connected to the main body, and configured to allow the wearable measurement apparatus to be disposed on the body part.

15. The wearable measurement apparatus of claim 11, further comprising an adsorption sensor configured to measure an adsorption force that is imposed on the body part when the biometric signal sensor is in contact with the body part.

16. The wearable measurement apparatus of claim 15, further comprising a controller,
wherein the adsorption sensor comprises a displacement sensor configured to measure a displacement of the sensor elastic part and a displacement of the main-body elastic part, and
the controller is configured to determine the adsorption force, based on the measured displacement of the sensor elastic part, the measured displacement of the main-body elastic part, a modulus of elasticity of the sensor elastic part, and a modulus of elasticity of the main-body elastic part.

17. The wearable measurement apparatus of claim 15, further comprising a display configured to display the adsorption force.

18. The wearable measurement apparatus of claim 11, further comprising a controller configured to determine whether the biometric signal is within a normal range.

19. The wearable measurement apparatus of claim 11, further comprising a step-difference control portion configured to adjust the step difference between the bottom surface of the biometric signal sensor and the bottom surface of the support member.

20. The wearable measurement apparatus of claim 1, wherein the main-body elastic part comprises a first spring that directly contacts the bottom surface of the main body and directly contacts the support member, and
the sensor elastic part comprises a second spring that directly contacts the bottom surface of the main body and directly contacts the top surface of the biometric signal sensor.

21. The wearable measurement apparatus of claim 1, wherein the sensor elastic part is further configured to form the step difference such that a first distance between the bottom surface of the biometric signal sensor and the bottom surface of the main body is greater than a second distance between the bottom surface of the support member and the bottom surface of the main body.

22. A wearable measurement apparatus comprising:
a main body comprising a display,
a support member configured to contact a body part of a user;
a main-body elastic part interposed between a bottom surface of the main body and the support member, and configured to elastically support the support member against the main body;
a biometric signal sensor disposed apart from the main-body elastic part, and configured to detect a biometric signal from the body part; and
a sensor elastic part directly contacting the bottom surface of the main body and directly contacting a top surface of the biometric signal sensor, and configured to:
for a step difference between a bottom surface of the biometric signal sensor and a bottom surface of the support member; and
elastically support the biometric signal sensor against the main body,
wherein the sensor elastic part is disposed such that the bottom surface of the biometric signal sensor is positioned lower than the bottom surface of the support member,
wherein the wearable measurement apparatus further comprises a step-difference control portion configured to adjust the step difference between the bottom surface of the biometric signal sensor and the bottom surface of the support member, and
wherein the step-difference control portion comprises:
a lifting block having a bottom surface coupled to a top surface of the sensor elastic part, and configured to move up and down the sensor elastic part and the biometric signal sensor; and
a control instrument having a bottom surface coupled to a top surface of the lifting block, and having a top surface coupled to the bottom surface of main body, the control instrument being configured to move up and down the lifting block.

* * * * *